United States Patent [19]

Lee et al.

[11] Patent Number: 5,008,190
[45] Date of Patent: Apr. 16, 1991

[54] **METHOD FOR PRODUCTION OF L-PHENYLALANINE BY RECOMBINANT *E. COLI***

[75] Inventors: Sae Bae Lee; Chan H. Won; Chung Park; Bun S. Lim, all of Seoul, Rep. of Korea

[73] Assignee: Miwon Co., Ltd., Seoul, Rep. of Korea

[21] Appl. No.: 120,461

[22] Filed: Nov. 13, 1987

[30] Foreign Application Priority Data

Mar. 26, 1987 [KR] Rep. of Korea ............... 87-2816

[51] Int. Cl.$^5$ ............... C12P 13/22; C12N 15/52; C12N 1/21; C12N 15/70
[52] U.S. Cl. ............... 435/108; 435/69.1; 435/71.2; 435/170; 435/172.1; 435/172.3; 435/252.33; 435/320.1; 435/849; 536/27; 935/6; 935/8; 935/9; 935/14; 935/22; 935/29; 935/33; 935/39; 935/43; 935/59; 935/60; 935/61; 935/66; 935/72; 935/73
[58] Field of Search ............ 435/108, 172.1, 172.3, 435/69.1, 71.2, 170, 252.33, 320, 849; 935/66, 73, 6, 8, 9, 14, 22, 29, 33, 39, 43, 59, 60, 61, 66, 72, 73; 536/27

[56] References Cited

U.S. PATENT DOCUMENTS 4,681,852 7/1987 Tribe ............... 435/108
4,839,286 6/1989 Backman ............... 435/108

OTHER PUBLICATIONS

Shimatake et al., Nature, vol. 292, pp. 128–131, (1981).
Renaut et al., 1983, *Gene*, 22:103–113.

Primary Examiner—Richard A. Schwartz
Assistant Examiner—Richard C. Peet
Attorney, Agent, or Firm—Birch, Stewart, Kolasch & Birch

[57] ABSTRACT

An *E. coli* which can produce phenylalanine and which has an optimum phenylalanine production capability at a temperature between 30° C. and 35° C., and a process for preparing L-phenylalanine by use of the novel *E. coli*. The novel *E. coli* is designated MWPEC 13-60 (ATCC 67459).

13 Claims, 3 Drawing Sheets

METHOD FOR PRODUCTION OF L-PHENYLALANINE BY RECOMBINANT *E. COLI*

CROSS REFERENCE TO RELATED APPLICATION

This application is related to application Ser. No. 07/120,148 entitled "A Method For Production Of L-Phenylalanine By Recombinant *E. Coli* ATCC 67460" (Attorney Docket No. 961-102P) filed concurrently herewith which is hereby incorporated by reference.

BACKGROUND OF THE INVENTION

1. Field of the Invention

The present invention relates to a method for production of L-phenylalanine by recombinant *Escherichia coli* (*E. coli*). More particularly, the present invention relates to a novel *E. coli* containing a gene for the production of L-phenylalanine and a process for the production of L-phenylalanine by use of the novel microbe.

2. Description of the Prior Art

L-phenylalanine is a kind of essential amino acid and can be used for the synthetic production of ASPARTAME ®, a sweetening agent. There are many known methods for production of L-phenylalanine by use of microbes. For example, Japanese Kokai Nos. 37-6345 and 60-160,890 disclose a method for production of L-phenylalanine by use of Brevibacterium or *Corynebacterium sp.* which require tyrosine. Japanese Kokai 55-165,797 discloses a similar method by use of *E. coli* which requires tyrosine and which is resistant against tryptophan analogues. However, such prior art processes are not particularly suited for L-phenylalanine production on an industrial scale. Furthermore, these processes produce low yields of L-phenylalanine.

Accordingly, it is known that a prior process for manufacturing a product is to amplify copy numbers of a gene which codes for a rate-limiting enzyme in a specific process by genetic engineering techniques. However, in many cases over expression of a gene in a cell leads to deletion of the gene in a plasmid or lysis of a cell which causes the cell to die. There are many methods which properly control the expression of the plasmid. For example, an inducer like IPTG (isopropyl thio-galactoside) was used in the lac operator system to control lac operon and alkaline phosphatase gene (refer to Itakma, A. et al, Science, 198, 1056, (1977), Miyanohava, A. et al; Proc. Natl. Acad. Sci. U.S.A., 80, 1 (1983)).

Also, there is a temperatupe shift method which uses the repressor cI 857 of a phage. Normally, under 37° C. the repressor is active and inhibits the operator so that transcription does not occur, but at a temperature higher than 37° C., the repressor becomes inactive and no longer inhibits the operator so that the gene under control of repressor is expressed.

SUMMARY OF THE INVENTION

Accordingly, it is an object of the present invention to provide a novel *E. coli* which can produce phenylalanine and which has an optimum phenylalanine production capability at a temperature of 30° to 35° C., preferably 30° to 32° C. The *E. coli* may be transformed with a plasmid containing genes which produce enzymes in the pathway of L-phenylalanine biosynthesis. The plasmid may contain a temperature sensitive repressor whereby optimum expression of the plasmid is accomplished at 30°–35° C. as compared with more than 38° C. of the prior art. The plasmid may be the plasmid W11 containing a Kanamycin resistance gene, a pheA gene and a aroF gene. The restriction enzymes PstI, EcoRI and HindIII can be used to make the plasmid. The restriction enzymes AflIII, HaeII, BamHI, BglII and DraIII may also be used to make the plasmid. A preferred *E. coli* of the present invention is MWPEC 13-60 (ATCC 67459) or a mutant thereof which possesses the same desirable phenylalanine production properties.

The present invention is also directed to a replicable recombinant plasmid which is capable of transforming an *E. coli* to produce a transformed *E. coli* having an optimum phenylalanine production capability at a temperature of 30°–35° C. The plasmid preferably contains the pheA and aroF genes and a temperature sensitive promoter which controls the expression of said genes.

The present invention is also directed to a method for the production of phenylalanine which comprises cultivating the *E. coli* of the present invention in a culture medium. The cultivation is preferably carried out at a temperature of 30° to 35° C., more preferably 30° to 32° C.. The culture medium will contain a primary food source such as sugar and other essential nutrients. The sugar may be glucose or a hydrolyzed mixture of glucose, fructose and sucrose. The method may also comprise the steps of aerating and agitating the culture media and recovering phenylalanine from the culture media. The phenylalanine may also be purified.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

The aroF and pheA genes for use in L-phenylalanine production are derived from *E. coli* MWEC 101-5 (KAIST, KCTC 8234p) by a shot gun method. At this time, the *E. coli* MWEC 101-5 is released from the control of the living synthetic metabolism. At this time the $P_R$-$P_L$ promoter of the lambda phage is involved in the process for increasing expression of the plasmid.

Figure 1:
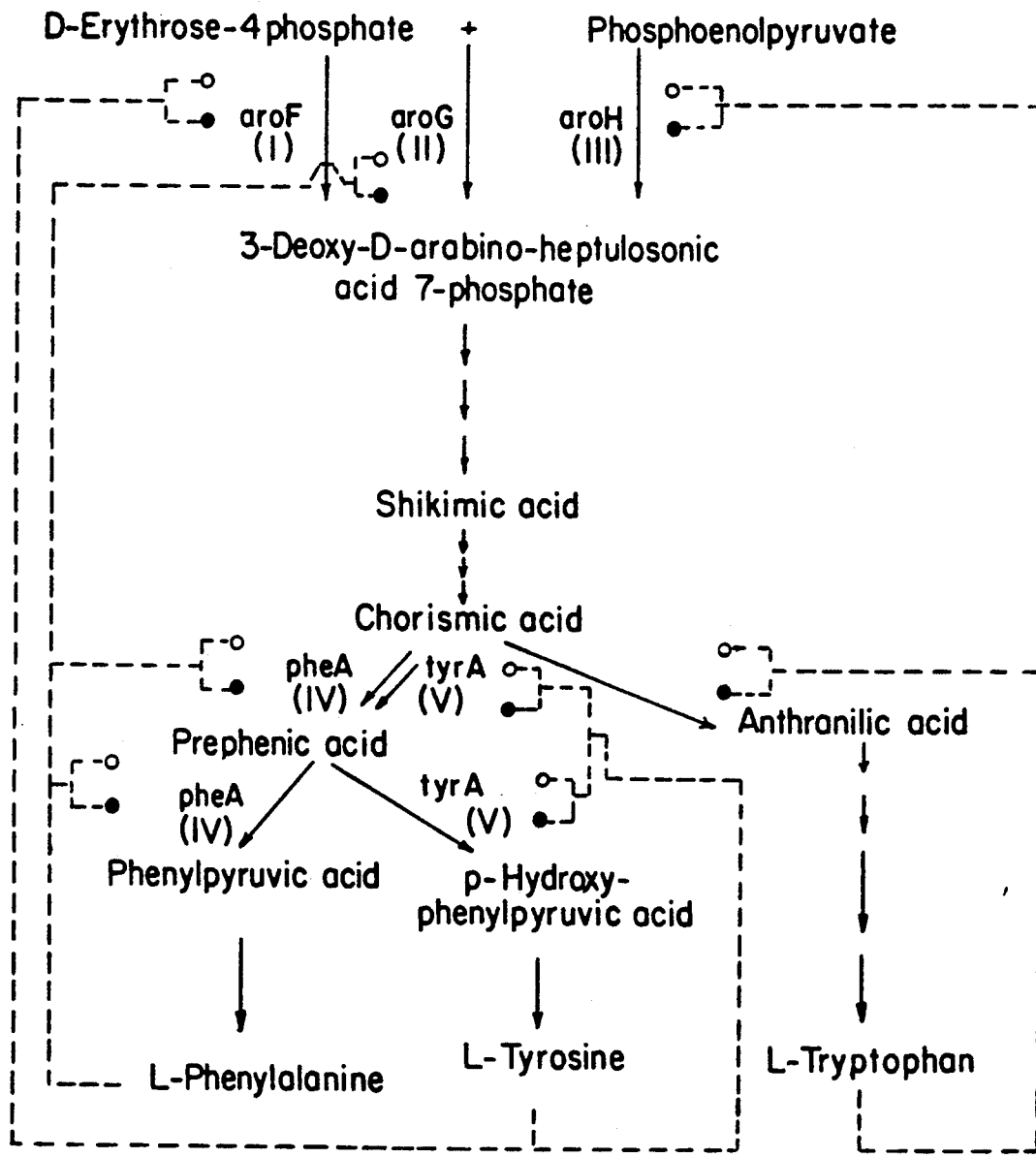
FIG. 1 illustrates the metabolic pathways for biosynthesis of aromatic amino acids in a *E. coli;*
Figure 2:
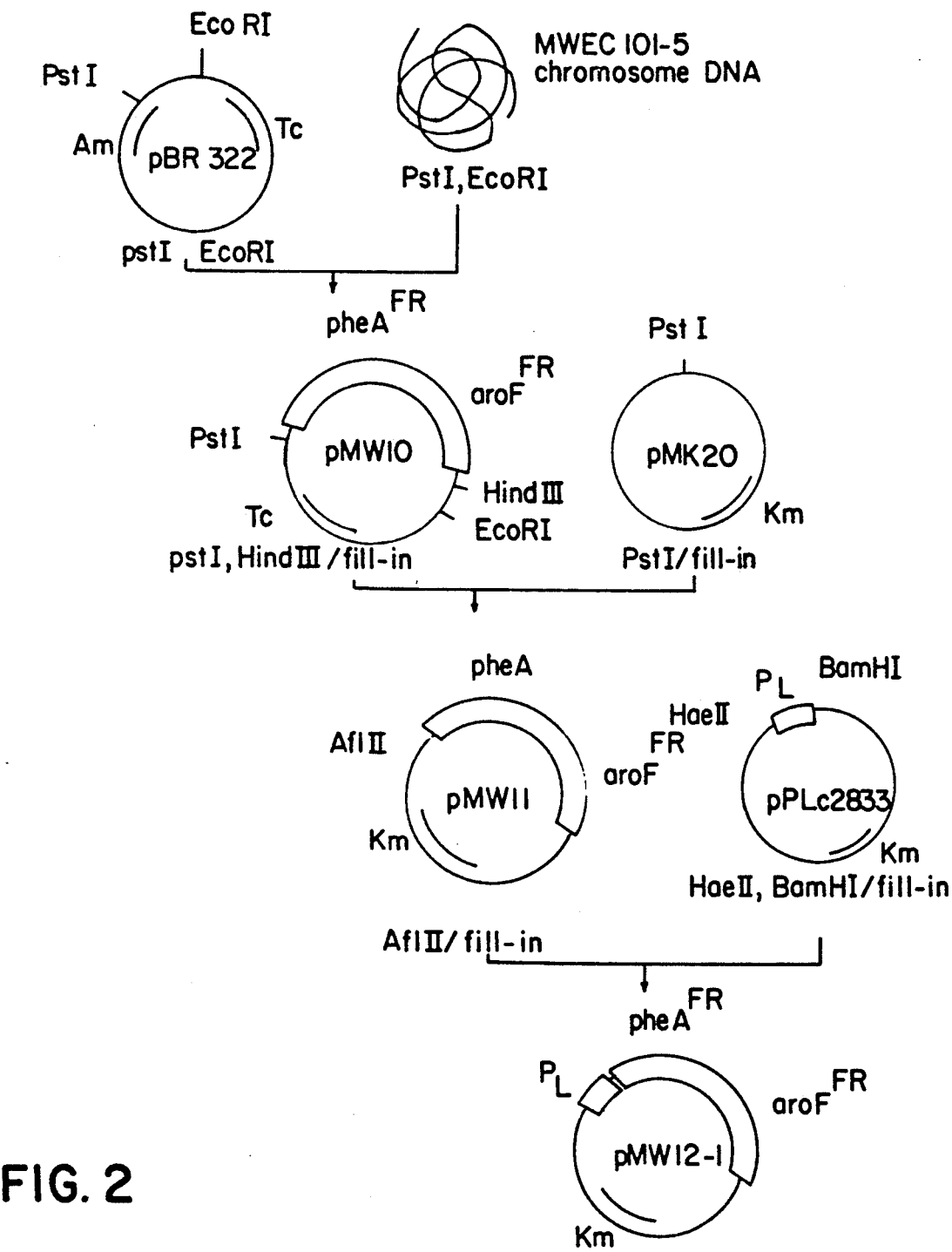
FIG. 2 illustrates steps for preparing a recombinant plasmid pMW12 and its restriction map.

Referring now in detail to the drawings for the purpose of illustrating the present invention, as shown in FIG. 1, the biosynthetic pathway of L-phenylalanine by use of the recombinant plasmid is controlled by enzyme action in *E. coli* cells. In FIG. 1, "I" is the DAHP synthase isoenzyme which is coded for by the aroF gene (tyrosine repressible); "II" is the DAHP synthase isoenzyme which is coded for by the aroG gene (phenylalanine repressible); "III" is the DAHP synthase isoenzyme which is coded for by the aroH gene (tryptophan repressible); "IV" is chorismate mutase P-prephenate dehydratase; "V" is chorismate mutase T-prephenate dehydrogenase; "●" is feedback inhibition "○" is feedback repression. One of the enzymes which controls the reaction is chorismate mutase P-prephenate dehydratase. One of the other enzymes which controls the reaction is the enzyme, 3-deoxy-D-arabino-heptulosonate-7-phosphate synthase (DAHP synthase). The DAHP synthase exists as three isoenzymes which are coded for by the aroF, aroG and aroH genes, respectively.

The general method for preparing the plasmid is described in Recombinant DNA Methodology (Jo-Anne R. Dillion, Anwar Nasim, Earle R. Nestmann) and Molecular Cloning (T. Maniatis, E. F. Fritsch, J. Sambrook).

The novel microbe, E. coli MWPEC 13-60, according to the present invention can be prepared as follows:

After MWEC 101-5 strain is cultivated and agitated in LB culture media (1% of bactotryptone, 0.5% of bactoyeast extract, 1% of sodium chloride, pH 7.4) at 37° C. for 15 hours, the cells are harvested. The chromosomal DNA (cDNA) was isolated by CsCl density gradient centrifugation method. Thereafter, the cDNA is purified by butanol treatment and dialysis.

Plasmids from E. coli HB101/pBR322, E. coli pPLC2833, E. coli HB101/pTR262 and E. coli HB101/pMK20 to be utilized in the present invention are also isolated and purified by the above-mentioned process steps. The cDNA is digested with EcoRI in medium salt restriction enzyme buffer (50 mM of sodium chloride, 10 mM of tris (pH 7.5), 10 mM of magnesium chloride, and 1 mM of dithiothreitol) at 37° C. for 1 hour. The restriction enzyme is inactivated in a conventional manner and the cDNA is further digested with the restriction enzyme PstI. A 4-7 kb fragment is recovered in 0.7% by weight of Agarose gel to be a target gene. The plasmid pBR322 is also digested by the above-mentioned restriction enzymes EcoRI and PstI. The digested plasmid pBR322 is mixed with the 4-7 kb gene fragment produced from E. coli MWEC 101-5 in an amount of 1:3. The digested plasmid and gene fragment are combined with each other in T4DNA ligase buffer solution (0.5M of tris (pH 7.4), 0.1M of magnesium chloride, 0.1M of dithiothreitol, 10 mM of spermidine, 10 mM of ATP, 1 mg/ml of bovine serum albumin) at 12°-14° C. for 12 hours.

The ligation mixture containing the combined recombinant plasmid is used to transform the phenylalanine auxotroph (pheA-deficiency strain) MWEC 203-7 by the calcium chloride method of Nogard. The transformed strain is maintained in MM culture media (10 g of glucose, 4 g of ammonium sulfate, 2 g of potassium phosphate, 0.5 g of magnesium sulfate, 20 mg of ferrous chloride, 10 mg of manganese chloride, 1 mg of thiamine hydrochloride salt, 0.5 g of fumaric acid, 1 l of distilled water, pH 7.4) at 37° C. for 1 hour. The treated strain is plated onto an agar MM culture media containing 15 μg/ml of tetracycline and is cultivated for 10 days. The recombinant strain which grows on MM is selected. The plasmid pMW10 is isolated from the selected strain and digested with the restriction enzyme, HindIII, partially digested again with the restriction enzyme PstI, and the restriction enzymes are inactivated.

A desired gene fragment containing the pheA and aroF genes is separated from 0.7% agarose gel.

T4 DNA polymerase and dNTP mixture solution (25 mM of dATP, 25 mM of dGTP, 25 mM of dCTP and 25 mM of dTTP) are added to the plasmid to convert the sticky ends to blunt ends.

Plasmid pMK20 containing Kanamycin antibiotic resistance gene (Km) is treated with PstI and is added to the T4DNA polymerase and the dNTp mixture solution to convert its sticky ends to blunt ends.

The PheA deficient strain, MWEC 203-7 is transformed according to the same method as mentioned above. The recombinant plasmid pMW11 is separated from cultivated strains which grew on MM in agar media containing 50 μg/ml kanamycin.

The plasmid pPLc2833 containing the $P_L$ promoter was treated with the restriction enzymes BamHI, HaeII and a 0.2 kb $P_L$ fragment was recovered on 2% agarose gel.

The recombinant plasmid pMW11 was digested with AflII and is then treated with DNA polymerase to form blunt ends at both ends.

The $P_L$ fragment is added to the treated pMWII and ligated to produce a recombinant plasmid. The recombinant plasmid is used to transform the MWEC 203-7 strain.

A pMW12 recombinant plasmid is separated from the transformed recombinant strain. The pMW12 recombinant plasmid is larger than pMW11 plasmid by 0.2 kb.

After, the plasmid pTR262 having a plasmid containing a repressor ($cI_{857}$) and a promoter ($P_R$) is genetically altered by treatment with hydroxylamine hydrochloride and UV irradiation. The treated plasmid is used to transform MWEC 101-6 strain.

The transformed strain is cultivated in LB Agar media which contains 15 μg/ml of tetracycline at 33° C. The growing colony is selected and is transferred to the LB agar media containing 15 μg/ml of tetracycline at 28° C. for 24 hours. Thereafter, the pTR262-10 containing the temperature-sensitive repressor is separated from non-growing colony.

The pMW12 recombinant plasmid is digested with DraIII and a blunt ends are formed by T4DNA polymerase. The pTR262-10 plasmid is digested with PstI and BglII to produce a fragment having cI and $P_R$.

After recovering the cI and $P_R$ fragment from 0.9% by weight Agarose gel, blunt ends are formed at both ends by DNA polymerase (the Klenow fragment of E. coli). T4DNA ligase is added to the treated product to produce a recombinant plasmid (pMW13). The plasmid pMW13 is used to transform the host strain MWEC 101-6 through the Norgard method. The transformed strain is cultivated in the LB agar media which contains kanamycin (50 μg/ml) and isolated a novel strain MWPEC 13-60 for use in manufacturing the L-phenylalanine. The novel strain MWPEC 13-60 was deposited at the American Type Culture Collection on July 14, 1987 in accordance with the conditions of the Budapest Treaty and was assigned deposit number ATCC 67459.

The biochemical properties of the novel strain MWPEC 13-60 are the same as that of host strain MWEC 101-6. However, the yield of L-phenylalanine and stability of the novel strain MWPEC 13-60 is increased when compared with the parent strain as follows (Tables I and II):

TABLE I

| cultivating temperature | Yield of L-phenylalanine (g/l) | |
|---|---|---|
| | MWEC 101-6 | MWPEC 13-60 |
| 30° C. | 23.6 | 28.9 |
| 32° C. | 24.8 | 42.8 |
| 34° C. | 16.4 | 39.6 |
| 36° C. | 14.5 | 20.7 |
| 38° C. | 8.0 | 6.2 |

The above data was obtained by following the procedures reported in Example 2.

TABLE II

Stability of recombinant plasmid

| Strain | culture media | Survival Ratio Unit (%) Cultivation time (hours) | | | | |
|---|---|---|---|---|---|---|
| | | 0 | 24 | 48 | 72 | 96 |
| MWEC 101-6 | LB km agar | 0 | 0 | 0 | 0 | 0 |
| | LB agar | 100 | 100 | 100 | 100 | 100 |
| MWPEC 13-60 | LB km agar | 100 | 100 | 100 | 97 | 95 |
| | LB agar | 100 | 100 | 100 | 100 | 100 |

After certain intervals of incubation in LB, samples were taken and plated on LB agar and LB kanamycin agar (50 μg/ml), respectively, and the colonies were counted after 24 hours.

The present invention will now be described in more detail in connection with the following examples which should be considered as being exemplary and not limiting the invention.

EXAMPLE 1

| (A) | Strain MWPEC-13-60 | | | |
|---|---|---|---|---|
| (B) | Seed Medium | | | |
| | Glucose | 5% | | |
| | Bacto-tryptone | 1% | | |
| | Bacto-yeast extract | 1% | | |
| | Sodium chloride | 0.1% | | |
| | Kanamycin | 10 mg/l | | |
| | pH | 7.0 | | |
| (C) | Fermentation Media | | | |
| | Glucose | 6% | Glutamic acid | 0.05% |
| | Calcium sulfate | 0.04% | Cobaltous chloride | 0.1 mg/l |
| | Ammonium sulfate | 2% | Zinc sulfate | 1 mg/l |
| | Sodium citrate | 0.05% | Manganous chloride | 2 mg/l |
| | Fumaric acid | 0.05% | Calcium chloride | 5 mg/l |
| | Magnesium chloride | 0.08% | Thiamine Hydrochloride salt | 10 mg/l |
| | Potassium phosphate, monobasic/ Potassium phosphate, dibasic | 0.1% | Nicotinic Acid | 10 mg/l |
| | Bactoyeast extract | 0.1% | pH | 7.0 |

(D) Fermentation Method 50 ml of the seed medium is charged into 500 ml of a test flask and heated at 120° C. for 20 minutes. The novel E. coli strain MWPEC 13-60 (ATCC 67459) is added to the flask and cultivated under 120 rpm at 30° C. for 16 hours. The fermentation media is prepared by the above-mentioned method.

After 5% of calcium carbonate is added to the fermentation media and 2 ml of seed medium is added thereto, the fermentation media is agitated and fermented at 32° C. for 35 hours. After finishing the fermentation, tne amount of L-phenylalanine is 12.46 g/l.

EXAMPLE 2

The (A) Strain, (B) Culture Media, and (C) Fermentation Media are the same as used in Example 1.

(D) Fermentation Method 50 ml of the culture media is charged into 500 ml of flask and heated at 120° C. for 20 minutes. The novel strain MWPEC 13-60 (ATCC 67459) is added to the flask and cultivated at 30° C. for 16 hours. 20 l of the fermentation media is charged into 50 l fermenter under 400 rpm and 0.75 vvm (oxygen rate) at 32° C. for 55 hours.

During fermentation, a pH of 7.0-7.2 is maintained by adding ammonia water and a 60% glucose solution to the fermentation apparatus two times when the level of glucose drops below 1%.

The total mol amount of glucose which is used in the fermentation is 160 g/l. L-phenylalanine is obtained in a concentration of 42.8 g/l. 1 l of fermentation solution is purified by a conventional method such as absorbing with ion-exchange resin and isolating with ammonium hydroxide to produce 38.52 g/l of L-phenylalanine as crude crystals.

EXAMPLE 3

Example 1 was repeated except that the glucose is replaced by a mixture of the sugars, fructose, glucose and sucrose which had been hydrolyzed by invertase. The amount of L-phenylalanine produced wa 43.7 g/l.

What is claimed is:

1. The E. coli MWPEC 13-60 (ATCC 67459) which has an optimum phenylalanine production capability at a temperature of 30° to 32° C.

2. A replicable recombinant plasmid which is capable of transforming an E. coli to produce a transformed E. coli having an optimum phenylalanine production capability of 30° to 32° C., said plasmid being identified as the plasmid pMW 13 contained in E. coli MWPEC 13-60 (ATCC 67459).

3. A process for production of phenylalanine which comprises: cultivating the E. coli of claim 1 in a culture medium.

4. The process of claim 3, wherein the E. coli is cultivated at a temperature of 30° to 35° C.

5. The process of claim 4, wherein the temperature is 30° to 32° C.

6. The process of claim 3, wherein cultivation is conducted in the presence of sugar.

7. The process of claim 6, wherein the sugar is a hydrolyzed mixture of glucose, fructose and sucrose.

8. The process of claim 3, which further comprises recovering L-phenylalanine from the culture media.

9. The process of claim 3, which further comprises aerating and agitating said culture media.

10. The process of claim 3, which further comprises purifying the recovered phenylalanine.

11. An E. coli containing the plasmid of claim 2.

Figure 3:
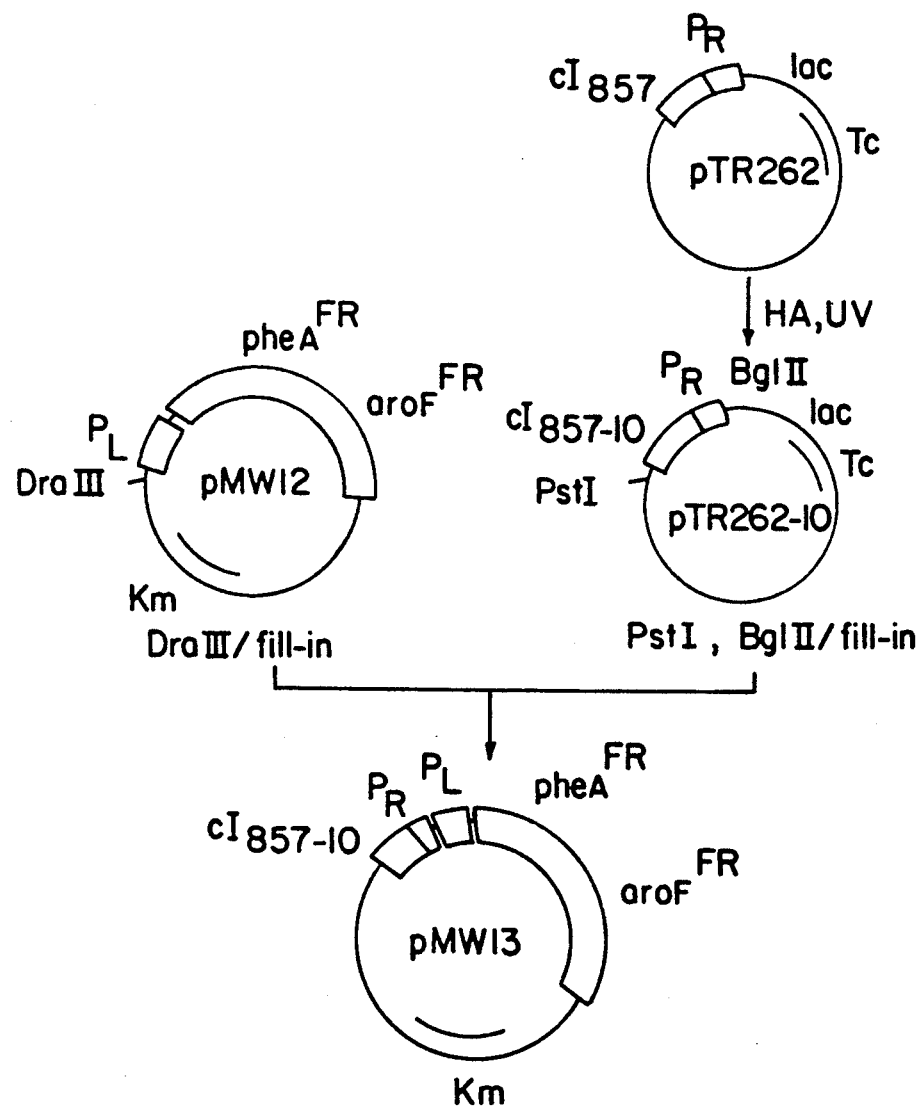
FIG. 3 illustrates steps for preparing a recombinant plasmid pMW13 and its restriction map.

12. A replicable recombinant plasmid which is capable of transforming an E. coli to produce a transformed E. coli having an optimum phenylalanine production capabiity of 30° to 32° C., said plasmid containing a temperature sensitive $CI_{857-10}$ repressor and having the structure of pMW 13 shown in FIG. 3.

13. An E. coli transformed with the plasmid of claim 12.

* * * * *